US008831896B2

United States Patent
Weinstein et al.

(10) Patent No.: US 8,831,896 B2
(45) Date of Patent: Sep. 9, 2014

(54) METER ELECTRONICS AND FLUID QUANTIFICATION METHOD FOR A FLUID BEING TRANSFERRED

(75) Inventors: Joel Weinstein, Boulder, CO (US); Steven M. Jones, Erie, CO (US)

(73) Assignee: Micro Motion, Inc., Boulder, CO (US)

( * ) Notice: Subject to any disclaimer, the term of this patent is extended or adjusted under 35 U.S.C. 154(b) by 442 days.

(21) Appl. No.: 13/382,212

(22) PCT Filed: Feb. 1, 2010

(86) PCT No.: PCT/US2010/022743
§ 371 (c)(1),
(2), (4) Date: Jan. 4, 2012

(87) PCT Pub. No.: WO2011/008307
PCT Pub. Date: Jan. 20, 2011

(65) Prior Publication Data
US 2012/0096923 A1    Apr. 26, 2012

Related U.S. Application Data

(60) Provisional application No. 61/225,025, filed on Jul. 13, 2009.

(51) Int. Cl.
*G01F 17/00* (2006.01)
*G01N 11/16* (2006.01)
*G01F 1/84* (2006.01)
*G01F 1/74* (2006.01)
*G01F 23/00* (2006.01)

(52) U.S. Cl.
CPC .............. *G01F 1/8436* (2013.01); *G01N 11/16* (2013.01); *G01F 1/74* (2013.01)

USPC ................... 702/50; 702/51; 702/52; 702/53; 702/54

(58) Field of Classification Search
CPC ....... G01F 1/74; G01F 1/8436; G01F 1/8486; G01F 1/8431; G01F 52/0007
USPC ...................................................... 702/50–56
See application file for complete search history.

(56) References Cited

U.S. PATENT DOCUMENTS 5,594,180 A  *  1/1997  Carpenter et al.  ....... 73/861.356
6,327,914 B1    12/2001  Dutton
(Continued)

FOREIGN PATENT DOCUMENTS

| RU | 2247331       | 2/2005 |
| WO | 0019175 A1    | 4/2000 |
| WO | 2007042051 A1 | 4/2007 |

*Primary Examiner* — Phuong Huynh
(74) *Attorney, Agent, or Firm* — The Ollila Law Group LLC (57) ABSTRACT

Meter electronics (20) for quantifying a fluid being transferred is provided. The meter electronics (20) includes an interface (201) configured to communicate with a flowmeter assembly of a vibratory flowmeter and receive a vibrational response and a processing system (203) coupled to the interface (201). The processing system (203) is configured to measure a mass flow and a density for a predetermined time portion of the fluid transfer, determine if the fluid transfer is non-aerated during the predetermined time portion, if the predetermined time portion is non-aerated then add a mass-density product to an accumulated mass-density product and add the mass flow to an accumulated mass flow, and determine a non-aerated mass-weighted density for the fluid transfer by dividing the accumulated mass-density product by the accumulated mass flow.

44 Claims, 4 Drawing Sheets

(56) References Cited

U.S. PATENT DOCUMENTS

| | | |
|---|---|---|
| 6,347,293 B1 | 2/2002 | Cunningham et al. |
| 2004/0031328 A1* | 2/2004 | Henry et al. ............... 73/861.18 |
| 2007/0131024 A1 | 6/2007 | Drahm |
| 2007/0198221 A1* | 8/2007 | James et al. .................. 702/187 |
| 2008/0184813 A1 | 8/2008 | Patten et al. |

* cited by examiner

METER ELECTRONICS AND FLUID QUANTIFICATION METHOD FOR A FLUID BEING TRANSFERRED

BACKGROUND OF THE INVENTION

1. Field of the Invention

The present invention relates to a vibratory flowmeter and method, and more particularly, to a meter electronics and fluid quantification method for a fluid being transferred.

2. Statement of the Problem

Vibrating conduit sensors, such as Coriolis mass flowmeters and vibrating densitometers, typically operate by detecting motion of a vibrating conduit that contains a flowing material. Properties associated with the material in the conduit, such as mass flow, density and the like, can be determined by processing measurement signals received from motion transducers associated with the conduit. The vibration modes of the vibrating material-filled system generally are affected by the combined mass, stiffness and damping characteristics of the containing conduit and the material contained therein.

A typical Coriolis mass flowmeter includes one or more conduits that are connected inline in a pipeline or other transport system and convey material, e.g., fluids, slurries, emulsions, and the like, in the system. Each conduit may be viewed as having a set of natural vibration modes, including for example, simple bending, torsional, radial, and coupled modes. In a typical Coriolis mass flow measurement application, a conduit is excited in one or more vibration modes as a material flows through the conduit, and motion of the conduit is measured at points spaced along the conduit. Excitation is typically provided by an actuator, e.g., an electromechanical device, such as a voice coil-type driver, that perturbs the conduit in a periodic fashion. Mass flow rate may be determined by measuring time delay or phase differences between motions at the transducer locations. Two such transducers (or pickoff sensors) are typically employed in order to measure a vibrational response of the flow conduit or conduits, and are typically located at positions upstream and downstream of the actuator. The two pickoff sensors are connected to electronic instrumentation. The instrumentation receives signals from the two pickoff sensors and processes the signals in order to derive a mass flow rate measurement, among other things. Vibratory flowmeters, including Coriolis mass flowmeters and densitometers, therefore employ one or more flow tubes that are vibrated in order to measure a fluid.

Bunkering refers to the practice of storing and transferring marine fuel oils, which have come to be known as bunker fuels. For ship fueling, large amounts of fuel may be temporarily stored in a barge or other container for the purpose of transferring fuel from shore to a ship. A bunker may be located on a dock or other port facility, or may be carried by a barge or other refueling vehicle. During bunkering, the fuel measurement usually comprises an empty-full-empty batching process, allowing gas to become entrained in the fuel.

Prior art fuel oil bunkering methods are based on volumetric tank measurements and a reference density typically obtained by laboratory sample. Look-up tables and reference density measurements are traditionally used to calculate the total mass of the delivered bunker fuel, in conjunction with a tank level measurement or dip tape measurement. Prior art measurement accuracy depends on many factors, including temperature, pressure, the presence or absence of entrained gas, dip tape measurement error or uncertainty, tank volume uncertainty, accuracy of conversion tables, human error, and how well the density sample represents the average batch density, for example. Further, heavy fuel oil (HFO) tends to stratify over time, so components may separate and have different densities, viscosities, etc.

While mass flow total is the most important measurement for a fuel transfer operation, the density and viscosity are also desired, as they are important indications of the quality or grade of the fuel oil. Generally, the higher the density and viscosity the lower the quality of fuel delivered. Knowledge of density and viscosity is essential for ensuring that the ideal fuel for a particular engine is used. In addition, a customer will want to determine how much of a fluid transfer is aerated. Such a determination can indicate whether the fuel is being intentionally aerated in order to increase the apparent volume of the fuel being delivered.

In the prior art, the current method for determining the bunker fuel's density and viscosity is to take a sample during the bunkering operation and send it to a laboratory for analysis. Unfortunately, laboratory analysis typically takes several days and the fuel will be on the ship and being used by that time. Further, fuel oil tends to stratify in tanks, leaving the lower grade fuel with the highest viscosity and density at the bottom of the tank and the higher quality fuel at the top. A single sample cannot capture the average density or viscosity of an entire batch.

ASPECTS OF THE INVENTION

In one aspect of the invention, meter electronics for quantifying a fluid being transferred comprises:
an interface configured to communicate with a flowmeter assembly of a vibratory flowmeter and receive a vibrational response; and
a processing system coupled to the interface and configured to:
measure a mass flow ($\dot{m}_i$) and a density ($\rho_i$) for a predetermined time portion ($t_i$) of the fluid transfer;
determine if the fluid transfer is non-aerated during the predetermined time portion ($t_i$);
if the predetermined time portion ($t_i$) is non-aerated, then add a mass-density product ($\dot{m}_i \rho_i$) to an accumulated mass-density product ($\dot{m}\rho_{accum}$) and add the mass flow ($\dot{m}_i$) to an accumulated mass flow ($\dot{m}_{accum}$); and
determine a non-aerated mass-weighted density ($\rho_{mass\text{-}weighted}$) for the fluid transfer by dividing the accumulated mass-density product ($\dot{m}\rho_{accum}$) by the accumulated mass flow ($\dot{m}_{accum}$).

Preferably, determining the non-aerated mass-weighted density ($\rho_{mass\text{-}weighted}$) for the fluid transfer occurs after a fluid transfer end signal is received.

Preferably, the processing system is further configured to compare a vibrational response of the predetermined time portion ($t_i$) to a predetermined aeration threshold and determine the predetermined time portion ($t_i$) to be aerated if the vibrational response fails the predetermined aeration threshold.

Preferably, the processing system is further configured to total aerated time portions to obtain an aerated transfer time ($t_{aerated}$), total all time portions ($t_i$) of the fluid transfer to obtain a total transfer time ($t_{total}$), and determine an aeration fraction ($t_{aerated}/t_{total}$) as the aerated transfer time ($t_{aerated}$) divided by the total transfer time ($t_{total}$).

Preferably, the processing system is further configured to total aerated mass flow ($\dot{m}_i$) values to obtain an aerated mass flow ($\dot{m}_{aerated}$), total all mass flow ($\dot{m}_i$) values to obtain a total mass flow ($\dot{m}_{tot}$), and determining an aeration fraction ($\dot{m}_{aerated}/\dot{m}_{tot}$) as the aerated mass flow ($\dot{m}_{aerated}$) divided by the total mass flow ($\dot{m}_{tot}$).

Preferably, the processing system is further configured to obtain a temperature ($T_i$) for the predetermined time portion ($t_i$), if the predetermined time portion ($t_i$) is non-aerated then add a mass-temperature product ($\dot{m}_i T_i$) to an accumulated mass-temperature product ($\dot{m}T_{accum}$), and determine a non-aerated mass-weighted temperature ($T_{mass-weighted}$) for the fluid transfer by dividing the accumulated mass-temperature product ($\dot{m}T_{accum}$) by the accumulated mass flow ($\dot{m}_{accum}$).

Preferably, the processing system is further configured to convert the non-aerated mass-weighted density ($\rho_{mass-weighted}$) to a standard density value using the non-aerated mass-weighted temperature ($T_{mass-weighted}$).

Preferably, the processing system is further configured to obtain a fluid viscosity ($\mu_i$) for the predetermined time portion ($t_i$), if the predetermined time portion ($t_i$) is non-aerated then add a mass-viscosity product ($\dot{m}_i \mu_i$) to an accumulated mass-viscosity product ($\dot{m}\mu_{accum}$), and determine a non-aerated mass-weighted viscosity ($\mu_{mass-weighted}$) for the fluid transfer by dividing the accumulated mass-viscosity product ($\dot{m}\mu_{accum}$) by the accumulated mass flow ($\dot{m}_{accum}$).

Preferably, the processing system is further configured to receive the viscosity ($\mu_i$) from an external source.

Preferably, the processing system is further configured to measure the viscosity ($\mu_i$) with the vibratory flowmeter.

Preferably, the processing system is further configured to obtain a fluid viscosity ($\mu_i$) for the predetermined time portion ($t_i$), if the predetermined time portion ($t_i$) is non-aerated then add a mass-viscosity product ($\dot{m}_i \mu_i$) to an accumulated mass-viscosity product ($\dot{m}\mu_{accum}$), determine a non-aerated mass-weighted viscosity ($\mu_{mass-weighted}$) for the fluid transfer by dividing the accumulated mass-viscosity product ($\dot{m}\mu_{accum}$) by the accumulated mass flow ($\dot{m}_{accum}$), and convert the non-aerated mass-weighted viscosity ($\mu_{mass-weighted}$) to a standard viscosity value using the non-aerated mass-weighted temperature ($T_{mass-weighted}$).

In one aspect of the invention, meter electronics for quantifying a fluid being transferred comprises:
an interface configured to communicate with a flowmeter assembly of a vibratory flowmeter and receive a vibrational response; and
a processing system coupled to the interface and configured to:
measure a mass flow ($\dot{m}_i$) for a predetermined time portion ($t_i$) of the fluid transfer;
obtain a fluid viscosity ($\mu_i$) for the predetermined time portion ($t_i$);
determine if the fluid transfer is non-aerated during the predetermined time portion ($t_i$);
if the predetermined time portion ($t_i$) is non-aerated, then add a mass-viscosity product ($\dot{m}_i \mu_i$) to an accumulated mass-viscosity product ($\dot{m}\mu_{accum}$) and add the mass flow ($\dot{m}_i$) to an accumulated mass flow ($\dot{m}_{accum}$); and
determine a non-aerated mass-weighted viscosity ($\mu_{mass-weighted}$) for the fluid transfer by dividing the accumulated mass-viscosity product ($\dot{m}\mu_{accum}$) by the accumulated mass flow ($\dot{m}_{accum}$).

Preferably, determining the non-aerated mass-weighted viscosity ($\mu_{mass-weighted}$) for the fluid transfer occurs after a fluid transfer end signal is received.

Preferably, the processing system is further configured to compare a vibrational response of the predetermined time portion ($t_i$) to a predetermined aeration threshold and determine the predetermined time portion ($t_i$) to be aerated if the vibrational response fails the predetermined aeration threshold.

Preferably, the processing system is further configured to total aerated time portions to obtain an aerated transfer time ($t_{aerated}$), total all time portions ($t_i$) of the fluid transfer to obtain a total transfer time ($t_{total}$), and determine an aeration fraction ($t_{aerated}/t_{total}$) as the aerated transfer time ($t_{aerated}$) divided by the total transfer time ($t_{total}$).

Preferably, the processing system is further configured to total aerated mass flow ($\dot{m}_i$) values to obtain an aerated mass flow ($\dot{m}_{aerated}$), total all mass flow ($\dot{m}_i$) values to obtain a total mass flow ($\dot{m}_{tot}$), and determining an aeration fraction ($\dot{m}_{aerated}/\dot{m}_{tot}$) as the aerated mass flow ($\dot{m}_{aerated}$) divided by the total mass flow ($\dot{m}_{tot}$).

Preferably, the processing system is further configured to obtain a temperature ($T_i$) for the predetermined time portion ($t_i$), if the predetermined time portion ($t_i$) is non-aerated then add a mass-temperature product ($\dot{m}_i T_i$) to an accumulated mass-temperature product ($\dot{m}T_{accum}$), and determine a non-aerated mass-weighted temperature ($T_{mass-weighted}$) for the fluid transfer by dividing the accumulated mass-temperature product ($\dot{m}T_{accum}$) by the accumulated mass flow ($\dot{m}_{accum}$).

Preferably, the processing system is further configured to convert the non-aerated mass-weighted viscosity ($\mu_{mass-weighted}$) to a standard viscosity value using the non-aerated mass-weighted temperature ($T_{mass-weighted}$).

Preferably, the processing system is further configured to measure a density ($\rho_i$) for the predetermined time portion ($t_i$), if the predetermined time portion ($t_i$) is non-aerated then add a mass-density product ($\dot{m}_i \rho_i$) to an accumulated mass-density product ($\dot{m}\rho_{accum}$) and determine a non-aerated mass-weighted density ($\rho_{mass-weighted}$) for the fluid transfer by dividing the accumulated mass-density product ($\dot{m}_{accum}$) by the accumulated mass flow ($\dot{m}_{accum}$).

Preferably, the processing system is further configured to measure a density ($\rho_i$) for the predetermined time portion ($t_i$), if the predetermined time portion ($t_i$) is non-aerated then add a mass-density product ($\dot{m}_i \rho_i$) to an accumulated mass-density product ($\dot{m}\rho_{accum}$) determine a non-aerated mass-weighted density ($\rho_{mass-weighted}$) for the fluid transfer by dividing the accumulated mass-density product ($\dot{m}\rho_{accum}$) by the accumulated mass flow ($\dot{m}_{accum}$), and convert the non-aerated mass-weighted density ($\rho_{mass-weighted}$) to a standard density value using the non-aerated mass-weighted temperature ($T_{mass-weighted}$).

Preferably, the processing system is further configured to receive the viscosity ($\mu_i$) from an external source.

Preferably, the processing system is further configured to measure the viscosity ($\mu_i$) with the vibratory flowmeter.

In one aspect of the invention, a fluid quantification method for a fluid being transferred comprises:
measuring a mass flow ($\dot{m}_i$) and a density ($\rho_i$) for a predetermined time portion ($t_i$) of the fluid transfer, with the measuring being performed by a vibratory flowmeter;
determining if the fluid transfer is non-aerated during the predetermined time portion ($t_i$);
if the predetermined time portion ($t_i$) is non-aerated, then adding a mass-density product ($\dot{m}_i \rho_i$) to an accumulated mass-density product ($\dot{m}\rho_{accum}$) and adding the mass flow ($\dot{m}_i$) to an accumulated mass flow ($\dot{m}_{accum}$); and
determining a non-aerated mass-weighted density ($\rho_{mass-weighted}$) for the fluid transfer by dividing the accumulated mass-density product ($\dot{m}\rho_{accum}$) by the accumulated mass flow ($\dot{m}_{accum}$).

Preferably, determining the non-aerated mass-weighted density ($\rho_{mass-weighted}$) for the fluid transfer occurs after a fluid transfer end signal is received.

Preferably, determining if the fluid transfer is non-aerated comprises comparing a vibrational response of the predetermined time portion ($t_i$) to a predetermined aeration threshold and determining the predetermined time portion ($t_i$) to be aerated if the vibrational response fails the predetermined aeration threshold.

Preferably, further comprising totaling aerated time portions to obtain an aerated transfer time ($t_{aerated}$), totaling all time portions ($t_i$) of the fluid transfer to obtain a total transfer time ($t_{total}$), and determining an aeration fraction ($t_{aerated}/t_{total}$) as the aerated transfer time ($t_{aerated}$) divided by the total transfer time ($t_{total}$).

Preferably, further comprising totaling aerated mass flow ($\dot{m}_i$) values to obtain an aerated mass flow ($\dot{m}_{aerated}$), totaling all mass flow ($\dot{m}_i$) values to obtain a total mass flow ($\dot{m}_{tot}$), and determining an aeration fraction ($\dot{m}_{aerated}/\dot{m}_{tot}$) as the aerated mass flow ($\dot{m}_{aerated}$) divided by the total mass flow ($\dot{m}_{tot}$).

Preferably, further comprising obtaining a temperature ($T_i$) for the predetermined time portion ($t_i$), if the predetermined time portion ($t_i$) is non-aerated then adding a mass-temperature product ($\dot{m}_i T_i$) to an accumulated mass-temperature product ($\dot{m}T_{accum}$), and determining a non-aerated mass-weighted temperature ($T_{mass-weighted}$) for the fluid transfer by dividing the accumulated mass-temperature product ($\dot{m}T_{accum}$) by the accumulated mass flow ($\dot{m}_{accum}$).

Preferably, further comprising converting the non-aerated mass-weighted density ($\rho_{mass-weighted}$) to a standard density value using the non-aerated mass-weighted temperature ($T_{mass-weighted}$).

Preferably, further comprising obtaining a viscosity ($\mu_i$) for the predetermined time portion ($t_i$), if the predetermined time portion ($t_i$) is non-aerated then adding a mass-viscosity product ($\dot{m}_i \mu_i$) to an accumulated mass-viscosity product ($\dot{m}\mu_{accum}$) and determining a non-aerated mass-weighted viscosity ($\mu_{mass-weighted}$) for the fluid transfer by dividing the accumulated mass-viscosity product ($\dot{m}\mu_{accum}$) by the accumulated mass flow ($\dot{m}_{accum}$).

Preferably, obtaining the viscosity ($\mu_i$) comprises receiving the viscosity ($\mu_i$) from an external source.

Preferably, obtaining the viscosity ($\mu_i$) comprises measuring the viscosity ($\mu_i$) with the vibratory flowmeter.

Preferably, further comprising obtaining a viscosity ($\mu_i$) for the predetermined time portion ($t_i$), if the predetermined time portion ($t_i$) is non-aerated then adding a mass-viscosity product ($\dot{m}_i \mu_i$) to an accumulated mass-viscosity product ($\dot{m}\mu_{accum}$), determining a non-aerated mass-weighted viscosity ($\mu_{mass-weighted}$) for the fluid transfer by dividing the accumulated mass-viscosity product ($\dot{m}\mu_{accum}$) by the accumulated mass flow ($\dot{m}_{accum}$), and converting the non-aerated mass-weighted viscosity ($\mu_{mass-weighted}$) to a standard viscosity value using the non-aerated mass-weighted temperature ($T_{mass-weighted}$).

In one aspect of the invention, a fluid quantification method for a fluid being transferred comprises:

measuring a mass flow ($\dot{m}_i$) for a predetermined time portion ($t_i$) of the fluid transfer, with the measuring being performed by a vibratory flowmeter;

obtaining a viscosity ($\mu_i$) for the predetermined time portion ($t_i$);

determining if the fluid transfer is non-aerated during the predetermined time portion ($t_i$);

if the predetermined time portion ($t_i$) is non-aerated, then adding a mass-viscosity product ($\dot{m}_i \mu_i$) to an accumulated mass-viscosity product ($\dot{m}\mu_{tot}$) and add the mass flow ($\dot{m}_i$) to an accumulated mass flow ($\dot{m}_{accum}$); and determining a non-aerated mass-weighted viscosity ($\mu_{mass-weighted}$) for the fluid transfer by dividing the accumulated mass-viscosity product ($\dot{m}\mu_{accum}$) by the accumulated mass flow ($\dot{m}_{accum}$).

Preferably, determining the non-aerated mass-weighted viscosity ($\mu_{mass-weighted}$) for the fluid transfer occurs after a fluid transfer end signal is received.

Preferably, determining if the fluid transfer is non-aerated comprises comparing a vibrational response of the predetermined time portion ($t_i$) to a predetermined aeration threshold and determining the predetermined time portion ($t_i$) to be aerated if the vibrational response fails the predetermined aeration threshold.

Preferably, further comprising totaling aerated time portions to obtain an aerated transfer time ($t_{aerated}$), totaling all time portions ($t_i$) of the fluid transfer to obtain a total transfer time ($t_{total}$), and determining an aeration fraction ($t_{aerated}/t_{total}$) as the aerated transfer time ($t_{aerated}$) divided by the total transfer time a ($t_{total}$).

Preferably, further comprising totaling aerated mass flow ($\dot{m}_i$) values to obtain an aerated mass flow ($\dot{m}_{aerated}$), totaling all mass flow ($\dot{m}_i$) values to obtain a total mass flow ($\dot{m}_{tot}$), and determining an aeration fraction ($\dot{m}_{aerated}/\dot{m}_{tot}$) as the aerated mass flow ($\dot{m}_{aerated}$) divided by the total mass flow ($\dot{m}_{tot}$).

Preferably, further comprising obtaining a temperature ($T_i$) for the predetermined time portion ($t_i$), if the predetermined time portion ($t_i$) is non-aerated then adding a mass-temperature product ($\dot{m}_i T_i$) to an accumulated mass-temperature product ($\dot{m}T_{accum}$), and determining a non-aerated mass-weighted temperature ($T_{mass-weighted}$) for the fluid transfer by dividing the accumulated mass-temperature product ($\dot{m}T_{accum}$) by the accumulated mass flow ($\dot{m}_{accum}$).

Preferably, further comprising converting the non-aerated mass-weighted viscosity ($\mu_{mass-weighted}$) to a standard viscosity value using the non-aerated mass-weighted temperature ($T_{mass-weighted}$).

Preferably, further comprising measuring a density ($\rho_i$) for the predetermined time portion ($t_i$), with the measuring being performed by the vibratory flowmeter, if the predetermined time portion ($t_i$) is non-aerated then adding a mass-density product ($\dot{m}_i \rho_i$) to an accumulated mass-density product ($\dot{m}\rho_{accum}$), and determining a non-aerated mass-weighted density ($\rho_{mass-weighted}$) for the fluid transfer by dividing the accumulated mass-density product ($\dot{m}\rho_{accum}$) by the accumulated mass flow ($\dot{m}_{accum}$).

Preferably, further comprising measuring a density ($\rho_i$) for the predetermined time portion ($t_i$), with the measuring being performed by the vibratory flowmeter, if the predetermined time portion ($t_i$) is non-aerated then adding a mass-density product ($\dot{m}_i \rho_i$) to an accumulated mass-density product ($\dot{m}\rho_{accum}$), determining a non-aerated mass-weighted density ($\rho_{mass-weighted}$) for the fluid transfer by dividing the accumulated mass-density product ($\dot{m}\rho_{accum}$) by the accumulated mass flow ($\dot{m}_{accum}$), and converting the non-aerated mass-weighted density ($\rho_{mass-weighted}$) to a standard density value using the non-aerated mass-weighted temperature ($T_{mass-weighted}$).

Preferably, obtaining the viscosity ($\mu_i$) comprises receiving the viscosity ($\mu_i$) from an external source.

Preferably, obtaining the viscosity ($\mu_i$) comprises measuring the viscosity ($\mu_i$) with the vibratory flowmeter.

DETAILED DESCRIPTION OF THE INVENTION

FIGS. 1-4 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
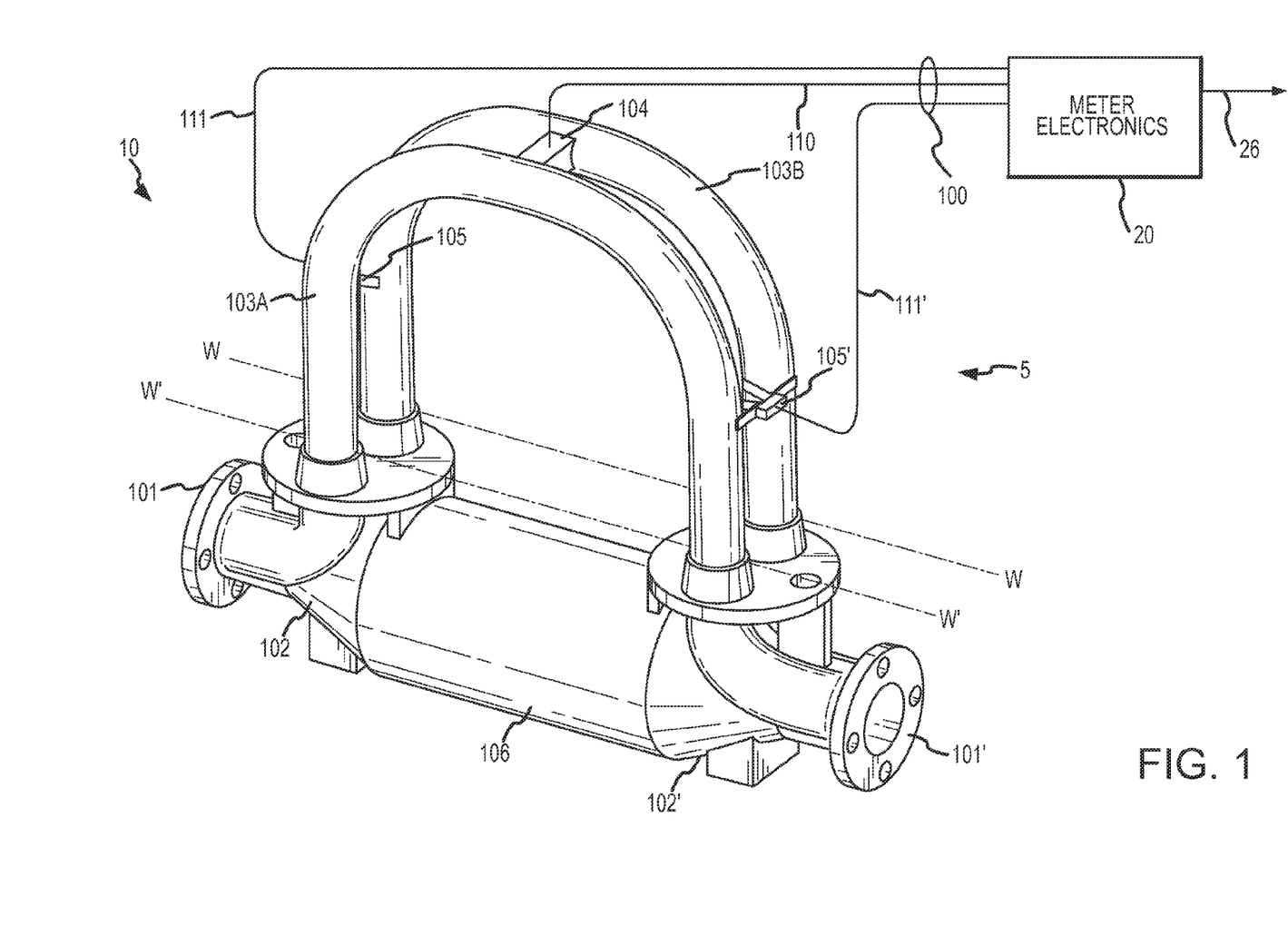
FIG. 1 shows a vibratory flowmeter according to the invention.

FIG. 1 shows a vibratory flowmeter 5 according to the invention. The vibratory flowmeter 5 comprises a flowmeter assembly 10 and meter electronics 20. The meter electronics 20 is connected to the meter assembly 10 via leads 100 and is configured to provide measurements of one or more of a density, mass flow rate, volume flow rate, totalized mass flow, temperature, or other measurements or information over a communication path 26. The vibratory flowmeter 5 can comprise a Coriolis mass flow meter. In addition, it should be recognized that the vibratory flowmeter 5 can alternatively comprise a vibratory densitometer. It should be apparent to those skilled in the art that the vibratory flowmeter can comprise any manner of vibratory flowmeter, regardless of the number of drivers, pick-off sensors, flow conduits, or the operating mode of vibration.

The flowmeter assembly 10 includes a pair of flanges 101 and 101', manifolds 102 and 102', a driver 104, pick-off sensors 105 and 105', and flow conduits 103A and 103B. The driver 104 and the pick-off sensors 105 and 105' are connected to the flow conduits 103A and 103B.

The flanges 101 and 101' are affixed to the manifolds 102 and 102'. The manifolds 102 and 102' can be affixed to opposite ends of a spacer 106 in some embodiments. The spacer 106 maintains the spacing between the manifolds 102 and 102' in order to prevent pipeline forces from being transmitted to flow conduits 103A and 103B. When the flowmeter assembly 10 is inserted into a pipeline (not shown) which carries the flow fluid being measured, the flow fluid enters the flowmeter assembly 10 through the flange 101, passes through the inlet manifold 102 where the total amount of flow fluid is directed to enter the flow conduits 103A and 103B, flows through the flow conduits 103A and 103B and back into the outlet manifold 102', where it exits the meter assembly 10 through the flange 101'.

The flow fluid can comprise a liquid. The flow fluid can comprise a gas. The flow fluid can comprise a multi-phase fluid, such as a liquid including entrained gases and/or entrained solids.

The flow conduits 103A and 103B are selected and appropriately mounted to the inlet manifold 102 and to the outlet manifold 102' so as to have substantially the same mass distribution, moments of inertia, and elastic modules about the bending axes W-W and W'-W' respectively. The flow conduits 103A and 103B extend outwardly from the manifolds 102 and 102' in an essentially parallel fashion.

The flow conduits 103A and 103B are driven by the driver 104 in opposite directions about the respective bending axes W and W' and at what is termed the first out of phase bending mode of the vibratory flowmeter 5. The driver 104 may comprise one of many well known arrangements, such as a magnet mounted to the flow conduit 103A and an opposing coil mounted to flow conduit 103B. An alternating current is passed through the opposing coil to cause both conduits to oscillate. A suitable drive signal is applied by the meter electronics 20 to the driver 104 via the lead 110. Other driver devices are contemplated and are within the scope of the description and claims.

The meter electronics 20 receives sensor signals on the leads 111 and 111', respectively. The meter electronics 20 produces a drive signal on the lead 110 which causes the driver 104 to oscillate the flow conduits 103A and 103B. Other sensor devices are contemplated and are within the scope of the description and claims.

The meter electronics 20 processes the left and right velocity signals from the pick-off sensors 105 and 105' in order to compute a flow rate, among other things. The communication path 26 provides an input and an output means that allows the meter electronics 20 to interface with an operator or with other electronic systems. The description of FIG. 1 is provided merely as an example of the operation of a Coriolis flowmeter and is not intended to limit the teaching of the present invention.

The meter electronics 20 in one embodiment is configured to vibrate the flowtubes 103A and 103B. The vibration is performed by the driver 104. The meter electronics 20 further receives resulting vibrational signals from the pickoff sensors 105 and 105'. The vibrational signals comprise a vibrational response of the flowtubes 103A and 103B. The meter electronics 20 processes the vibrational response and determines a response frequency and/or phase difference. The meter electronics 20 processes the vibrational response and determines one or more flow measurements, including a mass flow rate and/or density of the flow fluid. Other vibrational response characteristics and/or flow measurements are contemplated and are within the scope of the description and claims.

In one embodiment, the flowtubes 103A and 103B comprise substantially U-shaped flowtubes, as shown. Alternatively, in other embodiments, the flowtubes can comprise substantially straight flowtubes. Additional flowmeter shapes and/or configurations can be used and are within the scope of the description and claims.

Figure 2:
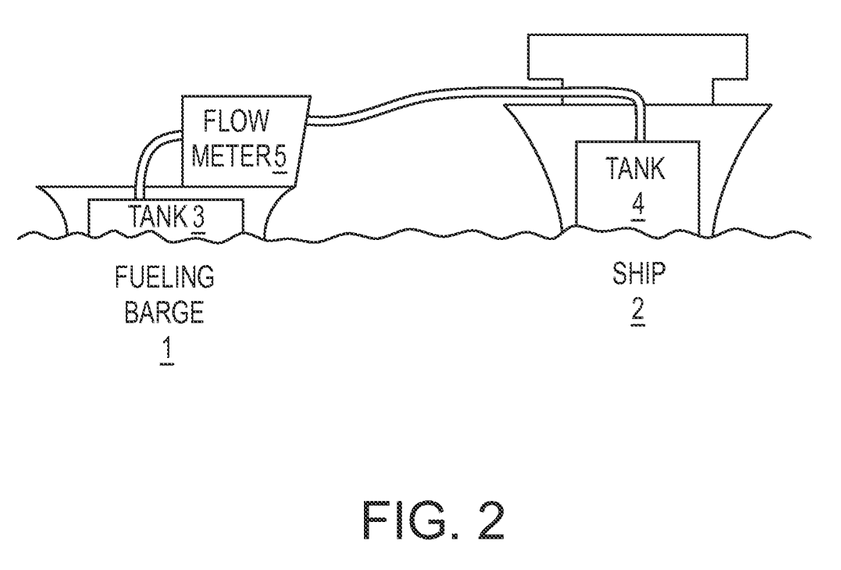
FIG. 2 shows a bunker fuel transfer according to the invention.

FIG. 2 shows a bunker fuel transfer according to the invention. The bunker fuel transfer comprises a transfer and metering of fuel from a first tank 3 to a second tank 4. In the figure, the bunker fuel is being transferred from a fueling barge 1 to a ship 2, but it should be understood that the transfer can comprise any fuel transfer. It should be understood that the transfer can comprise any fluid transfer. In addition, it should be understood that a flow meter may be installed on the barge, the ship, or in both locations.

Bunkering is generally known as the practice of storing and transferring marine fuel oils, which have come to be known as bunker fuels. For ship fueling, large amounts of fuel may be temporarily stored in a barge or other container for the purpose of transferring fuel from shore to a ship. A bunker may be located on a dock or other port facility, or may be carried by a barge or other refueling vehicle. During bunkering, the fuel measurement usually comprises an empty-full-empty batching process, allowing gas to become entrained in the fuel.

Bunker fuel comprises a relatively heavy petroleum derivative that is used in heating or in large industrial and/or marine engines. There are multiple grades of fuel that may comprise a bunker fuel. Bunker fuel is generally heavier and more viscous than gasoline or diesel. Bunker fuel therefore can settle and stratify during periods of storage.

It is desirable to meter the bunker fuel as it is being transferred. In the prior art, the metering typically comprises a volumetric metering. The volumetric metering can include using a volumetric flowmeter and/or measurements of filled or emptied tank volumes. However, the prior art volumetric metering has drawbacks. Volumetric metering incorrectly counts entrained gas as additional fuel oil. Aeration can increase the apparent volume of the bunker fuel and result in overcharging for the fuel, wherein the aerated bunker fuel has an increased volume but unchanged mass.

The aeration may be intentional, such as to reduce pumping costs or increase fuel revenues, or can unintentionally occur as a result of defective or improperly operating pumps, valves, or other devices which can cause cavitation or suck in air from the atmosphere. Aeration also frequently occurs during the process of stripping, which refers to the emptying of the fuel tanks of a barge. Near the end of a batch, the pump can suck gas into the process pipeline due to the low fluid volume left in the tanks. In barges without tank measurement equipment, it is necessary to completely drain a tank by stripping so as to use a shore-based supply reference measurement as the fuel transfer quantity.

Another drawback of volumetric metering is that bunker fuel may separate and stratify during holding, wherein heavier components settle to the bottom. As a result, bunker fuel quality and/or energy content may vary during a bunker fuel transfer.

Marine fuel costs represent a major portion of a ship's operating cost. With increasing oil prices and increasing conservation efforts, careful fuel management has become vital for environmental and financial reasons.

Blending a combination of fuel components in exact proportions for use in the marine industry typically involves the combination of heavy fuel oil (HFO or Bunker C) and an intermediate fuel oil (IFO), which is available in a range of viscosities and sulfur contents. The International Standard Organization (ISO) has specifications for marine fuels for worldwide use onboard ships. Precision blending is very important due to increases in fuel prices, the danger of engine wear from different fuel grade burn temperatures, and the limitations associated with shipboard storage. Preload blending guarantees that a vessel receives fuel with optimal properties for the intended use of specific onboard engines, leading to reductions in engine NOx and Sox emissions. The blending of fuels pre-bunkering has also been increasing in popularity in the marine industry due to regulations discouraging the mixing of fuels onboard the vessel. Blending operations often require high accuracy and a meter which is relatively immune to entrained gas, making mass flow meters ideal.

Figure 3:
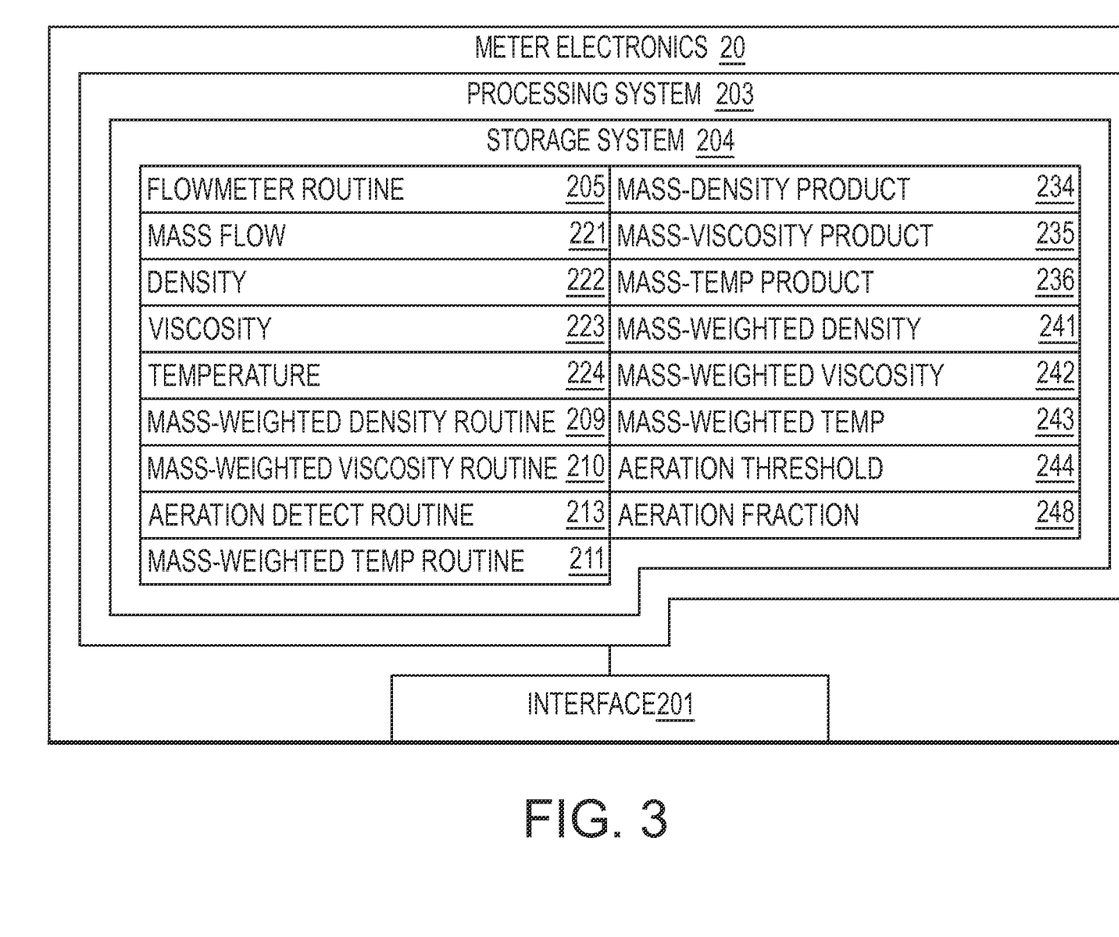
FIG. 3 is a block diagram of the meter electronics of the vibratory flowmeter according to the invention.

FIG. 3 is a block diagram of the meter electronics 20 of the vibratory flowmeter 5 according to the invention. In operation, the vibratory flowmeter 5 is used to quantify a fluid during a fluid transfer. The fluid can include a fuel. The vibratory flowmeter 5 can be used to measure a mass flow ($\dot{m}$) value and/or mass flow total ($\dot{m}_{tot}$) of a fluid transfer. The transfer in some embodiments is measured over a series of predetermined time portions ($t_i$). The predetermined time portions ($t_i$) can be uniform or non-uniform in duration. The predetermined time portions ($t_i$) can be chosen to generate a plurality of measurements during the transfer. The length of a predetermined time portion ($t_i$) can be chosen so as to capture accurate and representative values.

The vibratory flowmeter 5 generates a vibrational response. The vibrational response is received and processed by the meter electronics 20 to generate one or more fluid quantification values. The values can be monitored, recorded, and totaled.

The meter electronics 20 includes an interface 201, a processing system 203 in communication with the interface 201, and a storage system 204 in communication with the processing system 203. Although these components are shown as distinct blocks, it should be understood that the meter electronics 20 can be comprised of various combinations of integrated and/or discrete components.

The interface 201 is configured to communicate with the flowmeter assembly 10 of the vibratory flowmeter 5. The interface 201 may be configured to couple to the leads 100 (see FIG. 1) and exchange signals with the driver 104 and the pickoff sensors 105 and 105'. The interface 201 may be further configured to communicate over the communication path 26, such as to external devices.

The processing system 203 can comprise any manner of processing system. The processing system 203 is configured to retrieve and execute stored routines 205 in order to operate the vibratory flowmeter 5. The storage system 204 can store routines including a flowmeter routine 205, a mass-weighted density routine 209, a mass-weighted viscosity routine 210, a mass-weighted temperature routine 211, and an aeration detect routine 213. Other measurement/processing routines are contemplated and are within the scope of the description and claims. The storage system 204 can store measurements, received values, working values, and other information. In some embodiments, the storage system stores a mass flow ($\dot{m}$) 221, a density ($\rho$) 222, a viscosity ($\mu$) 223, a temperature (T) 224, a mass-density product ($\dot{m}\rho$) 234, a mass-viscosity product ($\dot{m}\mu$) 235, a mass-temperature product ($\dot{m}T$) 236, a mass-weighted density ($\rho_{mass\text{-}weighted}$) 241, a mass-weighted viscosity ($\mu_{mass\text{-}weighted}$) 242, a mass-weighted temperature ($T_{mass\text{-}weighted}$) 243, an aeration threshold 244, and an aeration fraction 248.

The flowmeter routine 205 can produce and store fluid quantifications and flow measurements. These values can comprise substantially instantaneous measurement values or can comprise totaled or accumulated values. For example, the flowmeter routine 205 can generate mass flow measurements and store them in the mass flow ($\dot{m}$) storage 221. The flowmeter routine 205 can generate density measurements and store them in the density ($\rho$) storage 222. The mass flow ($\dot{m}_i$) and density ($\rho_i$) values are determined from the vibrational response, as previously discussed and as known in the art. The mass flow ($\dot{m}_i$) can comprise a substantially instantaneous mass flow rate value, can comprise a mass flow rate sample, can comprise an averaged mass flow rate over the time portion ($t_i$), or can comprise an accumulated mass flow rate over the time portion ($t_i$). In addition, other mass flow quantifications are contemplated and are within the scope of the description and claims.

The flowmeter routine 205 can generate or receive temperature measurements and store them in the temperature (T) storage 224. The flowmeter routine 205 can generate or receive viscosity measurements and store them in the viscosity ($\mu$) storage 223.

The vibratory flowmeter 5 in some embodiments can be configured to perform viscosity measurements. One such vibratory flowmeter is disclosed in co-pending U.S. Patent Publication No. 2008/0184813, assigned to the current assignee. The 2008/0184813 patent publication is herein incorporated by reference.

Alternatively, in other embodiments the flowmeter routine 205 receives viscosity values from an external source and stores the received values in the viscosity ($\mu$) storage 223. The external source can be a separate viscosity meter, from an operator input, from a stored value, or other sources.

In some embodiments, the meter electronics 20 is configured to execute the mass-weighted density routine 209. The mass-weighted density routine 209 is configured to measure a mass flow ($\dot{m}_i$) and a density ($\rho_i$) for a predetermined time portion ($t_i$) of the fluid transfer, with the mass flow ($\dot{m}_i$) and density ($\rho_i$) measurements being performed by the vibratory flowmeter 5 through vibration of the flowmeter assembly 10, determine a mass-density product ($\dot{m}_i\rho_i$) for the predetermined time portion ($t_i$), accumulate the mass flow ($\dot{m}_i$) and the mass-density product ($\dot{m}_i\rho_i$) values into an accumulated mass flow ($\dot{m}_{accum}$) and an accumulated mass-density product ($\dot{m}\rho_{accum}$) for all non-aerated time portions of the fluid transfer, and determine a non-aerated mass-weighted density ($\rho_{mass\text{-}weighted}$) for the fluid transfer by dividing the accumulated mass-density product ($\dot{m}\rho_{accum}$) by the accumulated mass flow ($\dot{m}_{accum}$). The resulting non-aerated mass-weighted density value ($\rho_{mass\text{-}weighted}$) can be stored in the mass-weighted density storage 238. This processing may additionally generate the accumulated mass-density product ($\dot{m}\rho_{accum}$) that can be stored in the mass-density product storage 234. The processing therefore generates the mass-weighted density ($\rho_{mass\text{-}weighted}$) according to:

$$\rho_{mass\text{-}weighted} = \frac{\sum \dot{m}_i \rho_i}{\sum \dot{m}_i} = \frac{(\dot{m}_1\rho_1) + (\dot{m}_2\rho_2) + (\dot{m}_3\rho_3) + \ldots (\dot{m}_N\rho_N)}{\dot{m}_1 + \dot{m}_2 + \dot{m}_3 + \ldots \dot{m}_N} \quad (1)$$

The mass-weighted density ($\rho_{mass\text{-}weighted}$) can be similar to an average density, representing the density of the fluid transfer, but where only the density measurements for non-aerated time portions are taken into account. Density measurements from aerated time portions can be left out, as such aerated density measurements are likely to be inaccurate and unreliable. Also, the mass-weighted quantity is superior to a basic time-averaged or periodically sampled density because it represents a true average quantity with respect to the mass of fuel purchased. A time-averaged algorithm would be sensitive to variations in flow rate, and a periodic sampling system is sensitive to variation in density due to stratification of tanks.

It should be understood that a Coriolis meter operating in a typical batch mass totalizing manner can operate by adding every mass flow ($\dot{m}_i$) measurement into a total mass flow ($\dot{m}_{tot}$). This may be done because the mass of a gas is small and therefore aeration will usually not affect the accuracy of the mass flow measurements made by the vibratory flowmeter 5 being operated as a Coriolis mass flow meter. However, when the vibratory flowmeter 5 is operated as a densitometer or viscosity meter, aeration in the fluid can affect and degrade density and viscosity measurements (and possibly temperature measurements). For this reason, the mass-density, mass-viscosity, and/or mass-temperature products are not totaled during aeration time periods.

In some embodiments, the meter electronics 20 is configured to execute the mass-weighted viscosity routine 210. The mass-weighted viscosity routine 210 is configured to measure a mass flow ($\dot{m}_i$) and obtain a fluid viscosity ($\mu_i$) for a predetermined time portion ($t_i$) of the fluid transfer, with at least the mass flow ($\dot{m}_i$) measurement being performed by the vibratory flowmeter 5 through vibration of the flowmeter assembly 10, determine a mass-viscosity product ($\dot{m}_i\mu_i$) for the predetermined time portion ($t_i$), accumulate the mass flow ($\dot{m}_i$) and the mass-viscosity product ($\dot{m}_i\mu_i$) values into an accumulated mass flow ($\dot{m}_{accum}$) and an accumulated mass-viscosity product ($\dot{m}\mu_{accum}$) for all non-aerated predetermined time portions of the fluid transfer, and determine a non-aerated mass-weighted viscosity ($\mu_{mass\text{-}weighted}$) for the fluid transfer by dividing the accumulated mass-viscosity product ($\dot{m}\mu_{accum}$) by the accumulated mass flow ($\dot{m}_{accum}$). This non-aerated mass-weighted viscosity value ($\mu_{mass\text{-}weighted}$) can be stored in the mass-weighted viscosity storage 239. The viscosity measurements can reflect quality or grade of the flow fluid as it is transferred. This processing may additionally generate the accumulated mass-viscosity product ($\dot{m}\mu_{accum}$) that can be stored in the mass-viscosity product storage 235. The processing therefore generates the mass-weighted viscosity ($\mu_{mass\text{-}weighted}$) according to:

$$\mu_{mass\text{-}weighted} = \frac{\sum \dot{m}_i \mu_i}{\sum \dot{m}_i} \quad (2)$$

The mass-weighted viscosity ($\mu_{mass\text{-}weighted}$) can be similar to an average viscosity, representing the overall viscosity of the fluid transfer, but where only the viscosity measurements for non-aerated time portions are taken into account. Viscosity measurements from aerated time portions can be left out, as such aerated viscosity measurements are likely to be inaccurate and unreliable.

In some embodiments, the meter electronics 20 is configured to execute the mass-weighted temperature routine 211. The mass-weighted temperature routine 211 is configured to measure a mass flow ($\dot{m}_i$) and a temperature ($T_i$) for a predetermined time portion ($t_i$) of the fluid transfer, with at least the mass flow ($\dot{m}_i$) measurement being performed by the vibratory flowmeter 5 through vibration of the flowmeter assembly 10, determine a mass-temperature product ($\dot{m}_i T_i$) for the predetermined time portion ($t_i$), accumulate the mass flow ($\dot{m}_i$) and the mass-temperature product ($\dot{m}_i T_i$) values into an accumulated mass flow ($\dot{m}_{accum}$) and an accumulated mass-temperature product ($\dot{m}T_{accum}$) for all non-aerated predetermined time portions of the fluid transfer, and determine a non-aerated mass-weighted temperature ($T_{mass\text{-}weighted}$) for the fluid transfer by dividing the accumulated mass-temperature product ($\dot{m}T_{accum}$) by the accumulated mass flow ($\dot{m}_{accum}$). This non-aerated mass-weighted temperature value ($T_{mass\text{-}weighted}$) can be stored in the mass-weighted temperature storage 243. This processing may additionally generate the accumulated mass-temperature product ($\dot{m}T_{accum}$) that can be stored in the mass-temperature product storage 236. The processing therefore generates the mass-weighted temperature ($T_{mass\text{-}weighted}$) according to:

$$T_{mass\text{-}weighted} = \frac{\sum \dot{m}_i T_i}{\sum \dot{m}_i} \quad (3)$$

The mass-weighted temperature ($T_{mass\text{-}weighted}$) can be similar to an average temperature, representing the overall temperature of the fluid transfer, but where only the temperature measurements for non-aerated time portions are taken into account. Temperature measurements from aerated time portions can be left out.

In some embodiments, the meter electronics 20 is configured to execute the aeration detect routine 213. The aeration detect routine 213 processes flowmeter values in order to detect substantial aeration in a fluid transfer. The detection can be substantially continuously performed during the fluid transfer, such as during each time portion ($t_i$). The aeration detect routine 213 is configured to vibrate the flowmeter assembly 10 of a vibratory flowmeter 5 during the fluid transfer, compare a vibrational response of each time portion ($t_i$) of the fluid transfer to an aeration threshold 244, and determine that a time portion ($t_i$) is an aerated time portion where the vibrational response does not exceed the aeration threshold 244. The aeration threshold 244 comprises a range above which the fluid is considered to be non-aerated or is considered to be minimally (e.g., acceptably) aerated.

In some embodiments, the aeration threshold 244 comprises a drive gain threshold. A current drive gain is compared to the drive gain threshold. The drive gain quantifies the amount of response per a given drive input. The drive gain can comprise a pickoff response amplitude divided by a driver vibration amplitude, where the values can be instantaneous or can be averaged or integrated over the predetermined time portion ($t_i$). The drive gain will typically be stable at around ten to thirty percent for a pure liquid and will increase dramatically as entrained gas enters the flow fluid. If the drive gain fails the aeration threshold 244, then the meter electronics 20 can determine that the fluid is aerated. For example, the drive gain may fail the aeration threshold 244 if the drive gain exceeds the aeration threshold 244, as the drive gain may increase in value with the presence of aeration.

In some embodiments, the aeration threshold 244 comprises a minimum response amplitude. The minimum response amplitude relates to the vibrational response amplitude generated by a pickoff sensor 105 or 105'. It is known that the pickoff amplitude will decrease with entrained air in the flow fluid. If the pickoff amplitude fails the aeration threshold 244, then the meter electronics 20 can determine that the fluid is aerated. For example, the pickoff amplitude may fail the aeration threshold 244 if the pickoff amplitude is less than the aeration threshold 244, as the pickoff amplitude may decrease in value with the presence of aeration.

In some embodiments, the aeration threshold 244 comprises a minimum density threshold for the fluid. The predetermined aerated density threshold can comprise a level of acceptable aeration in the fluid, such as for air in a bunker fuel, for example. Consequently, the measured density ($\rho_i$) can be compared to the aeration threshold 244. If the measured density ($\rho_i$) fails the aeration threshold 244, then the meter electronics 20 can determine that the fluid is aerated. For example, the measured density ($\rho_i$) may fail the aeration threshold 244 if the measured density ($\rho_i$) is less than the aeration threshold 244, as the fluid density will decrease with aeration.

Aeration may be detected based on a damping estimate, found from the shape of a frequency response function for the drive mode of the flow meter. For example, the width of the drive mode peak in a frequency response graph can help determine whether gas is present. A wider peak indicates higher damping and therefore the presence of gas. Consequently, the damping estimate/drive mode peak width can be compared to the aeration threshold 244. If the damping estimate/drive mode peak width fails the aeration threshold 244, then the meter electronics 20 can determine that the fluid is aerated. For example, the damping estimate/drive mode peak width may fail the aeration threshold 244 if the damping estimate/drive mode peak width exceeds the aeration threshold 244, as the damping may increase in the presence of aeration.

Alternatively, a 3-dB down point may be used, which refers to the width of the peak at a specific off-resonant frequency which corresponds to a specific vibrational response amplitude. Consequently, the 3-dB down point can be compared to the aeration threshold 244. If the 3-dB down point fails the aeration threshold 244, then the meter electronics 20 can determine that the fluid is aerated. For example, the 3-dB down point may fail the aeration threshold 244 if the 3-dB down point is less than the aeration threshold 244, as the magnitude of the 3-dB down point may drop in the presence of aeration.

Flow noise increases with increasing aeration, and therefore it is also possible to detect the presence of gas by analysis of the standard deviations in the mass flow, density, or other measurements from a Coriolis meter. A high standard deviation can indicate an increase in aeration. Consequently, the standard deviation in the flow measurements due to flow noise (or other disturbances), can be compared to the aeration threshold 244. If the standard deviation fails the aeration threshold 244, then the meter electronics 20 can determine that the fluid is aerated. For example, the standard deviation may fail the aeration threshold 244 if the standard deviation exceeds the aeration threshold 244.

An aeration fraction is determined in some embodiments and stored in the aeration fraction storage 248. The aeration fraction denotes an amount of the fluid transfer that is aerated, and may serve as another fluid quality indicator. In some embodiments, the mass flow ($\dot{m}_i$) values can be totaled for time portions ($t_i$) of detected aeration. The aerated mass ($\dot{m}_{aerated}$) can be divided by the total mass ($\dot{m}_{tot}$) to provide an aeration mass fraction ($\dot{m}_{aerated}/\dot{m}_{tot}$), i.e., a measure of the amount of transferred mass that is aerated. Alternatively, the aerated time portions can be totaled and then divided by a total transfer time to generate an aeration time fraction, for example. Other aeration fraction quantifications are contemplated and are within the scope of the description and claims.

The mass measurement will provide a better and more accurate measurement of a fluid transfer than a volumetric flow, as a mass flow measurement will not be negatively affected by aeration of the fluid. The mass flow measurement can be used to derive a fluid transfer volume wherein the mass flow measurement can be cross-checked against a volume transfer measurement, a tank fill measurement, etc. The total mass measurement will provide a better and more accurate measurement of the energy content of the transferred fuel, in contrast to a volume measurement of the prior art. A prior art volume measurement will not take into account any expansion or contraction due to temperature or other ambient conditions. A prior art volume measurement will not take into account any aeration of the fuel.

Figure 4:
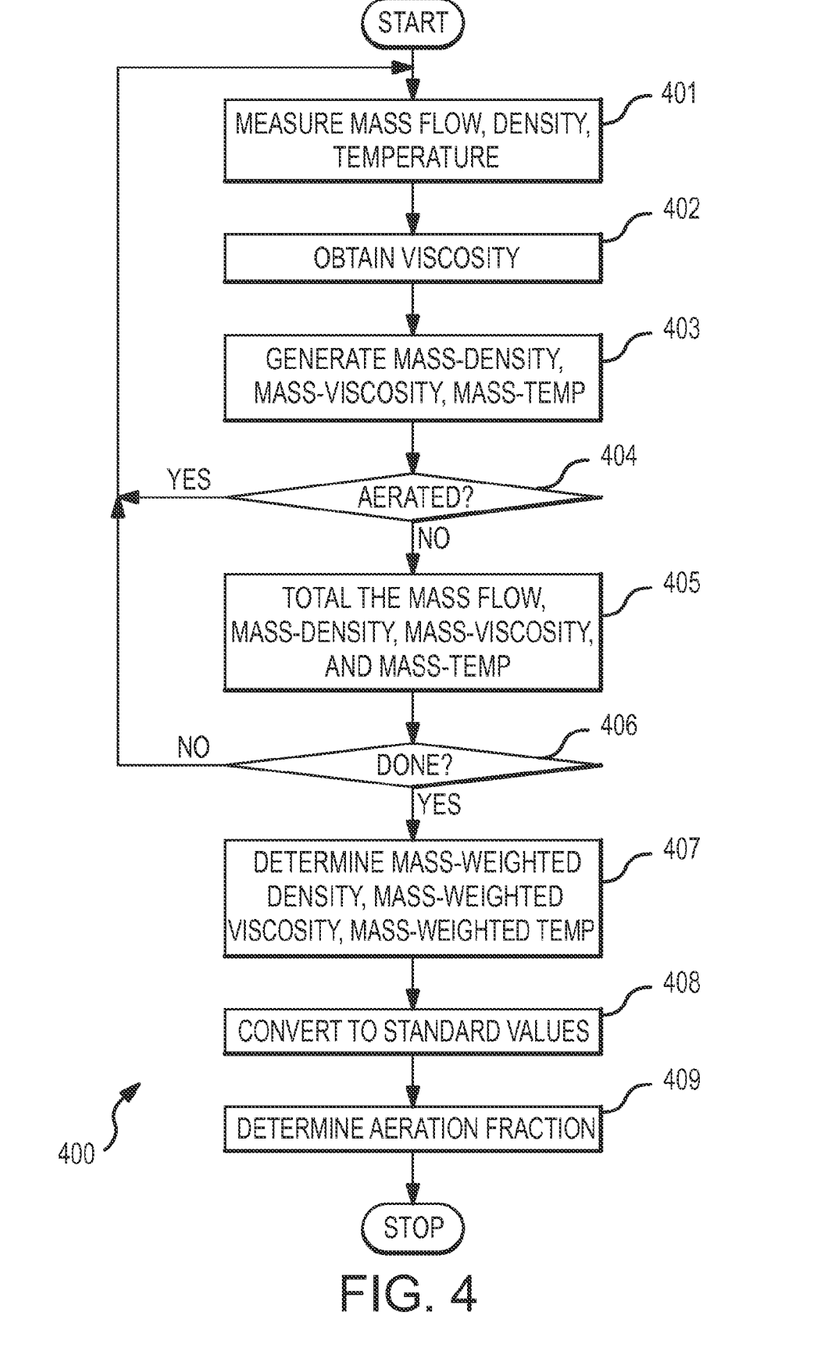
FIG. 4 is a flowchart of a fluid quantification method for a fluid being transferred according to the invention.

FIG. 4 is a flowchart 400 of a fluid quantification method for a fluid being transferred according to the invention. The method comprises taking measurements at predetermined time portions ($t_i$). In step 401, mass flow ($\dot{m}_i$), density ($\rho_i$), and temperature ($T_i$) values are measured for a current predetermined time portion ($t_i$). The mass flow ($\dot{m}_i$) and density ($\rho_i$) values are determined from the vibrational response, as previously discussed and as known in the art.

Step 401 can comprise a start of the fluid transfer process. In addition, step 401 can comprise an iterative measurement step obtained at any time during the fluid transfer process.

The predetermined time portions ($t_i$) can be of any desired length that will adequately characterize the fluid being transferred. The predetermined time portions ($t_i$) are preferably substantially uniform in length, but do not have to be uniform or consistent.

In step 402, a viscosity ($\mu_i$) value is obtained. The viscosity ($\mu_i$) may be measured. Alternatively, the viscosity ($\mu_i$) may be received from an external measurement source such as a viscometer or a differential pressure measurement across the flow meter or a length of pipe.

In step 403, a mass-density product ($\dot{m}_i\rho_i$) is generated from the mass flow ($\dot{m}_i$) and density ($\rho_i$) measurements. A mass-viscosity product ($\dot{m}_i\mu_i$) is generated from the mass flow ($\dot{m}_i$) and viscosity ($\mu_i$) measurements. A mass-temperature product ($\dot{m}_iT_i$) is generated from the mass flow ($\dot{m}_i$) and temperature ($T_i$) measurements. The mass flow ($\dot{m}_i$), density ($\rho_i$), mass-density product ($\dot{m}_i\rho_i$), mass-viscosity product ($\dot{m}_i\mu_i$), and mass-temperature product ($\dot{m}_iT_i$) values can be added into previous values and therefore accumulated. Alternatively, the mass flow ($\dot{m}_i$), density ($\rho_i$), mass-density product ($\dot{m}_i\rho_i$), mass-viscosity product ($\dot{m}_i\mu_i$), and mass-temperature product ($\dot{m}_iT_i$) values can be selectively accumulated, as discussed below.

In step 404, if the fluid transfer during the current time portion ($t_i$) is not substantially aerated, then the method proceeds to step 405. Otherwise, where the fluid is determined to be aerated, the method branches back to step 401 and the mass flow ($\dot{m}_i$), density ($\rho_i$), mass-density product ($\dot{m}_i\rho_i$), mass-viscosity product ($\dot{m}_i\mu_i$), and mass-temperature product ($\dot{m}_iT_i$) values are not accumulated. Instead, new values are obtained upon a next predetermined time portion ($t_{i+1}$). However, it should be understood that the measurements may be recorded in some manner and therefore may be available for other use, if desired.

In an alternative embodiment, if the fluid is determined to be substantially aerated, then the measurements may simply not be performed during the current time portion ($t_i$). In this embodiment, step 403 could be performed as a first step and would loop back on itself if aeration were detected, with the measuring/obtaining of steps 401, 402, and 403 being skipped in the event of aeration detection. The mass flow ($\dot{m}_i$), density ($\rho_i$), mass-density product ($\dot{m}_i\rho_i$), mass-viscosity product ($\dot{m}_i\mu_i$), and mass-temperature product ($\dot{m}_iT_i$) values could simply be neglected, saving processing time.

In step 405, the mass flow ($\dot{m}_i$), density ($\rho_i$), mass-density product ($\dot{m}_i\rho_i$), mass-viscosity product ($\dot{m}_i\mu_i$), and mass-temperature product ($\dot{m}_iT_i$) values are accumulated, added into respective running totals for the fluid transfer. The accumulated mass flow ($\dot{m}_{accum}$), when the fluid transfer is completed, in some embodiments may represent the mass of non-aerated fluid transferred. The total density ($\rho_{tot}$) can be processed when the fluid transfer is completed in order to determine a mean, average, weighted, or mass-weighted density of fluid transferred. The mass-weighted density is desirable because the fluid being transferred may not be uniform in nature. A measure or quantification of a density for the fluid transfer as a whole may be more useful than an averaged density. Moreover, elimination of the mass values and/or density values of an aerated portion or portions of the fluid transfer may avoid skewing or mis-characterizing the fluid. If the fluid is highly aerated, the density measurements will be affected. Not only will the quantity of delivered fluid decrease when aerated, but also the vibratory flowmeter will generate inaccurate density measurements due to the aeration.

This is an advantage of a mass flow measurement over a volume flow measurement. A volume flow measurement according to the prior art will measure a greater quantity of fluid being delivered, but an inaccurate quantity of fluid, if the fluid is aerated.

In step 406, if the method is done, i.e., the fluid transfer is complete, then the method proceeds to step 407. Otherwise, where the fluid transfer is not complete, the method branches back to step 401. In this manner, the measurement process is iteratively performed over the entire fluid transfer process.

The fluid transfer may be complete when a fluid transfer end signal is received in the vibratory flowmeter. The fluid transfer end signal may be received from an operator or from another device. Alternatively, the vibratory flowmeter can autonomously determine an end of the fluid transfer and generate the fluid transfer end signal. For example, the vibratory flowmeter can autonomously generate the fluid transfer end signal in some embodiments if the mass flow drops below a predetermined transfer threshold for more than a predetermined time period.

In step 407, where the fluid transfer is complete, values are determined for the fluid transfer as a whole. A non-aerated mass-weighted density ($\rho_{mass-weighted}$) can be determined for the fluid transfer. The non-aerated mass-weighted density ($\rho_{mass-weighted}$) comprises the accumulated mass-density product ($\dot{m}\rho_{accum}$) divided by the accumulated mass flow product ($\dot{m}_{accum}$). This can be represented by equation (1), above. The non-aerated mass-weighted density ($\rho_{mass-weighted}$) in some embodiments comprises a density generated from only the non-aerated fluid portions. The non-aerated mass-weighted density ($\rho_{mass-weighted}$) therefore comprises a more accurate density for the fluid when there is any aeration in the fluid. If the fluid is not determined to be aerated, then the mass-weighted density ($\rho_{mass-weighted}$) will substantially match an average density for the entire fluid transfer.

A non-aerated mass-weighted viscosity ($\mu_{mass-weighted}$) can be determined for the fluid transfer. The non-aerated mass-weighted viscosity ($\mu_{mass-weighted}$) comprises the accumulated mass-viscosity product ($\dot{m}\mu_{accum}$) divided by the accumulated mass flow ($\dot{m}_{accum}$). This can be represented by equation (2), above. The non-aerated mass-weighted viscosity ($\mu_{mass-weighted}$) in some embodiments comprises a viscosity generated from only the non-aerated fluid portions.

A non-aerated mass-weighted temperature ($T_{mass-weighted}$) can be determined for the fluid transfer. The non-aerated mass-weighted temperature ($T_{mass-weighted}$) comprises the accumulated mass-temperature product ($\dot{m}T_{accum}$) divided by the accumulated mass flow ($\dot{m}_{accum}$). This can be represented by equation (3), above. The non-aerated mass-weighted temperature ($T_{mass-weighted}$) in some embodiments comprises a temperature generated from only the non-aerated fluid portions.

In step 408, the non-aerated mass-weighted temperature ($T_{mass-weighted}$) can be used to perform temperature compensation. For example, the computed mass-weighted density ($\rho_{mass-weighted}$) can be temperature-compensated to generate a mass-weighted density value for a standard temperature. In addition or alternatively, the mass-weighted viscosity ($\mu_{mass-weighted}$) can also be temperature compensated. This can be done using known methods, such as by using a table or tables available from the American Petroleum Institute (API) for a bunker fuel or other fuel product, wherein the mass-weighted density and the mass-weighted temperature are used to produce a corresponding standard density value. The mass weighted viscosity and the mass-weighted temperature are used to produce a corresponding standard viscosity value. Such a table can be used to translate a value at a given temperature to the value at a reference temperature. The reference temperature value is useful for comparing the computed mass-weighted density and/or the computed mass-weighted viscosity to a standard value in order to judge the quality of the bunker fuel or other fluid. In this manner, the relative quality of the bunker fuel can be assessed, where if the computed mass-weighted density/viscosity deviates significantly from a standard value, then the quality of the bunker fuel (or other fluid) may be poor or unacceptable.

In step 409, an aeration fraction is determined, as previously discussed.

The meter electronics and fluid quantification method according to the invention can be employed according to any of the embodiments in order to provide several advantages, if desired. The meter electronics and fluid quantification method can generate a more reliable measurement of potentially aerated fluids. The meter electronics and fluid quantification method can generate a more accurate measurement of fluid properties, even if those properties vary throughout the batch. The resulting mass flow rate measurement is not affected by ambient temperature or pressure. The meter electronics and fluid quantification method can generate a more accurate measurement of fluid transfer, wherein the measurement is not affected by aeration. The meter electronics and fluid quantification method can detect aeration in the fluid. The meter electronics and fluid quantification method can generate a better measure of energy content of a fuel. The meter electronics and fluid quantification method can cross-check against a volume measurement/estimate. The meter electronics and fluid quantification method can generate measurements and records of fluid variation during transfer.

What is claimed is:

1. Meter electronics (20) for quantifying a fluid being transferred, the meter electronics (20) comprising an interface (201) configured to communicate with a flowmeter assembly of a vibratory flowmeter and receive a vibrational response and a processing system (203) coupled to the interface (201) and configured to measure a mass flow ($\dot{m}_i$) and a density ($\rho_i$) for a predetermined time portion ($t_i$) of the fluid transfer, with the processing system (203) being characterized by being configured to:

determine if the fluid transfer is non-aerated during the predetermined time portion ($t_i$);

if the predetermined time portion ($t_i$) is non-aerated, then add a mass-density product ($\dot{m}_i\rho_i$) to an accumulated mass-density product ($\dot{m}\rho_{accum}$) and add the mass flow ($\dot{m}_i$) to an accumulated mass flow ($\dot{m}_{accum}$); and determine a non-aerated mass-weighted density ($\rho_{mass-weighted}$) for the fluid transfer by dividing the accumulated mass-density product ($\dot{m}\rho_{accum}$) by the accumulated mass flow ($\dot{m}_{accum}$).

2. The meter electronics (20) of claim 1, with determining the non-aerated mass-weighted density ($\rho_{mass-weighted}$) for the fluid transfer occurring after a fluid transfer end signal is received.

3. The meter electronics (20) of claim 1, with the processing system (203) being further configured to:

compare a vibrational response of the predetermined time portion ($t_i$) to a predetermined aeration threshold; and determine the predetermined time portion ($t_i$) to be aerated if the vibrational response fails the predetermined aeration threshold.

4. The meter electronics (20) of claim 3, with the processing system (203) being further configured to:

total aerated time portions to obtain an aerated transfer time ($t_{aerated}$);

total all time portions ($t_i$) of the fluid transfer to obtain a total transfer time ($t_{total}$); and determine an aeration fraction ($t_{aerated}/t_{total}$) as the aerated transfer time ($t_{aerated}$) divided by the total transfer time ($t_{total}$).

5. The meter electronics (20) of claim 3, with the processing system (203) being further configured to:

total aerated mass flow ($\dot{m}_i$) values to obtain an aerated mass flow ($\dot{m}_{aerated}$);

total all mass flow ($\dot{m}_i$) values to obtain a total mass flow ($\dot{m}_{tot}$); and determine an aeration fraction ($\dot{m}_{aerated}/\dot{m}_{tot}$) as the aerated mass flow ($\dot{m}_{aerated}$) divided by the total mass flow ($\dot{m}_{tot}$).

6. The meter electronics (20) of claim 1, with the processing system (203) being further configured to:

obtain a temperature ($T_i$) for the predetermined time portion ($t_i$);

if the predetermined time portion ($t_i$) is non-aerated, then add a mass-temperature product ($\dot{m}_iT_i$) to an accumulated mass-temperature product ($\dot{m}T_{accum}$); and determine a non-aerated mass-weighted temperature ($T_{mass-weighted}$) for the fluid transfer by dividing the accumulated mass-temperature product ($\dot{m}T_{accum}$) by the accumulated mass flow ($\dot{m}_{accum}$).

7. The meter electronics (20) of claim 6, with the processing system (203) being further configured to convert the non-aerated mass-weighted density ($\rho_{mass-weighted}$) to a standard density value using the non-aerated mass-weighted temperature ($T_{mass-weighted}$).

8. The meter electronics (20) of claim 1, with the processing system (203) being further configured to:

obtain a fluid viscosity ($\mu_i$) for the predetermined time portion ($t_i$);

if the predetermined time portion ($t_i$) is non-aerated, then add a mass-viscosity product ($\dot{m}_i\mu_i$) to an accumulated mass-viscosity product ($\dot{m}\mu_{accum}$); and determine a non-aerated mass-weighted viscosity ($\mu_{mass-weighted}$) for the fluid transfer by dividing the accumulated mass-viscosity product ($\dot{m}\mu_{accum}$) by the accumulated mass flow ($\dot{m}_{accum}$).

9. The meter electronics (20) of claim 8, with the processing system (203) being further configured to receive the viscosity ($\mu_i$) from an external source.

10. The meter electronics (20) of claim 8, with the processing system (203) being further configured to measure the viscosity ($\mu_i$) with the vibratory flowmeter (5).

11. The meter electronics (20) of claim 6, with the processing system (203) being further configured to:

obtain a fluid viscosity ($\mu_i$) for the predetermined time portion ($t_i$);

if the predetermined time portion ($t_i$) is non-aerated, then add a mass-viscosity product ($\dot{m}_i\mu_i$) to an accumulated mass-viscosity product in ($\dot{m}\mu_{accum}$);

determine a non-aerated mass-weighted viscosity ($\mu_{mass-weighted}$) for the fluid transfer by dividing the accumulated mass-viscosity product ($\dot{m}\mu_{accum}$) by the accumulated mass flow ($\dot{m}_{accum}$); and convert the non-aerated mass-weighted viscosity ($\mu_{mass-weighted}$) to a standard viscosity value using the non-aerated mass-weighted temperature ($T_{mass-weighted}$).

12. Meter electronics (20) for quantifying a fluid being transferred, the meter electronics (20) comprising an interface (201) configured to communicate with a flowmeter assembly of a vibratory flowmeter and receive a vibrational response and a processing system (203) coupled to the interface (201) and configured to measure a mass flow ($\dot{m}_i$) for a predetermined time portion ($t_i$) of the fluid transfer, with the processing system (203) being characterized by being configured to:

obtain a fluid viscosity ($\mu_i$) for the predetermined time portion ($t_i$);

determine if the fluid transfer is non-aerated during the predetermined time portion ($t_i$);

if the predetermined time portion ($t_i$) is non-aerated, then add a mass-viscosity product ($\dot{m}_i\mu_i$) to an accumulated mass-viscosity product ($\dot{m}\mu_{accum}$) and add the mass flow ($\dot{m}_i$) to an accumulated mass flow ($\dot{m}_{accum}$); and determine a non-aerated mass-weighted viscosity ($\mu_{mass-weighted}$) for the fluid transfer by dividing the accumulated mass-viscosity product ($\dot{m}\mu_{accum}$) by the accumulated mass flow ($\dot{m}_{accum}$).

13. The meter electronics (20) of claim 12, with determining the non-aerated mass-weighted viscosity ($\mu_{mass-weighted}$) for the fluid transfer occurring after a fluid transfer end signal is received.

14. The meter electronics (20) of claim 12, with the processing system (203) being further configured to:
compare a vibrational response of the predetermined time portion ($t_i$) to a predetermined aeration threshold; and
determine the predetermined time portion ($t_i$) to be aerated if the vibrational response fails the predetermined aeration threshold.

15. The meter electronics (20) of claim 14, with the processing system (203) being further configured to:
total aerated time portions to obtain an aerated transfer time ($t_{aerated}$);
total all time portions ($t_i$) of the fluid transfer to obtain a total transfer time a ($t_{total}$); and
determine an aeration fraction ($t_{aerated}/t_{total}$) as the aerated transfer time ($t_{aerated}$) divided by the total transfer time ($t_{total}$).

16. The meter electronics (20) of claim 14, with the processing system (203) being further configured to:
total aerated mass flow ($\dot{m}_i$) values to obtain an aerated mass flow ($\dot{m}_{aerated}$);
total all mass flow ($\dot{m}_i$) values to obtain a total mass flow ($\dot{m}_{tot}$); and
determine an aeration fraction ($\dot{m}_{aerated}/\dot{m}_{tot}$) as the aerated mass flow ($\dot{m}_{aerated}$) divided by the total mass flow ($\dot{m}_{tot}$).

17. The meter electronics (20) of claim 12, with the processing system (203) being further configured to:
obtain a temperature ($T_i$) for the predetermined time portion ($t_i$);
if the predetermined time portion ($t_i$) is non-aerated, then add a mass-temperature product ($\dot{m}_i T_i$) to an accumulated mass-temperature product ($\dot{m}T_{accum}$); and
determine a non-aerated mass-weighted temperature ($T_{mass-weighted}$) for the fluid transfer by dividing the accumulated mass-temperature product ($\dot{m}T_{accum}$) by the accumulated mass flow ($\dot{m}_{accum}$).

18. The meter electronics (20) of claim 17, with the processing system (203) being further configured to convert the non-aerated mass-weighted viscosity ($\mu_{mass-weighted}$) to a standard viscosity value using the non-aerated mass-weighted temperature ($T_{mass-weighted}$).

19. The meter electronics (20) of claim 12, with the processing system (203) being further configured to:
measure a density ($\rho_i$) for the predetermined time portion ($t_i$);
if the predetermined time portion ($t_i$) is non-aerated, then add a mass-density product ($\dot{m}_i \rho_i$) to an accumulated mass-density product ($\dot{m}\rho_{accum}$); and
determine a non-aerated mass-weighted density ($\rho_{mass-weighted}$) for the fluid transfer by dividing the accumulated mass-density product ($\dot{m}\rho_{accum}$) by the accumulated mass flow ($\dot{m}_{accum}$).

20. The meter electronics (20) of claim 17, with the processing system (203) being further configured to:
measure a density ($\rho_i$) for the predetermined time portion ($t_i$);
if the predetermined time portion ($t_i$) is non-aerated, then add a mass-density product ($\dot{m}_i \rho_i$) to an accumulated mass-density product ($\dot{m}\rho_{accum}$);
determine a non-aerated mass-weighted density ($\rho_{mass-weighted}$) for the fluid transfer by dividing the accumulated mass-density product ($\dot{m}\rho_{accum}$) by the accumulated mass flow ($\dot{m}_{accum}$); and
convert the non-aerated mass-weighted density ($\rho_{mass-weighted}$) to a standard density value using the non-aerated mass-weighted temperature ($T_{mass-weighted}$).

21. The meter electronics (20) of claim 12, with the processing system (203) being further configured to receive the viscosity ($\mu_i$) from an external source.

22. The meter electronics (20) of claim 12, with the processing system (203) being further configured to measure the viscosity ($\mu_i$) with the vibratory flowmeter (5).

23. A fluid quantification method for a fluid being transferred, the method comprising measuring a mass flow ($\dot{m}_i$) and a density ($\rho_i$) for a predetermined time portion ($t_i$) of the fluid transfer, with the measuring being performed by a vibratory flowmeter, with the method being characterized by:
determining if the fluid transfer is non-aerated during the predetermined time portion ($t_i$);
if the predetermined time portion ($t_i$) is non-aerated, then adding a mass-density product ($\dot{m}_i \rho_i$) to an accumulated mass-density product ($\dot{m}\rho_{accum}$) and adding the mass flow ($\dot{m}_i$) to an accumulated mass flow ($\dot{m}_{accum}$); and
determining a non-aerated mass-weighted density ($\rho_{mass-weighted}$) for the fluid transfer by dividing the accumulated mass-density product ($\dot{m}\rho_{accum}$) by the accumulated mass flow ($\dot{m}_{accum}$).

24. The method of claim 23, with determining the non-aerated mass-weighted density ($\rho_{mass-weighted}$) for the fluid transfer occurring after a fluid transfer end signal is received.

25. The method of claim 23, with determining if the fluid transfer is non-aerated comprising:
comparing a vibrational response of the predetermined time portion ($t_i$) to a predetermined aeration threshold; and
determining the predetermined time portion ($t_i$) to be aerated if the vibrational response fails the predetermined aeration threshold.

26. The method of claim 25, further comprising:
totaling aerated time portions to obtain an aerated transfer time ($t_{aerated}$);
totaling all time portions ($t_i$) of the fluid transfer to obtain a total transfer time ($t_{total}$); and
determining an aeration fraction ($t_{aerated}/t_{total}$) as the aerated transfer time ($t_{aerated}$) divided by the total transfer time ($t_{total}$).

27. The method of claim 25, further comprising:
totaling aerated mass flow ($\dot{m}_i$) values to obtain an aerated mass flow ($\dot{m}_{aerated}$);
totaling all mass flow ($\dot{m}_i$) values to obtain a total mass flow ($\dot{m}_{tot}$); and
determine an aeration fraction ($\dot{m}_{aerated}/\dot{m}_{tot}$) as the aerated mass flow ($\dot{m}_{aerated}$) divided by the total mass flow ($\dot{m}_{tot}$).

28. The method of claim 23, further comprising:
obtaining a temperature ($T_i$) for the predetermined time portion ($t_i$);
if the predetermined time portion ($t_i$) is non-aerated, then adding a mass-temperature product ($\dot{m}_i T_i$) to an accumulated mass-temperature product ($\dot{m}T_{accum}$); and
determining a non-aerated mass-weighted temperature ($T_{mass-weighted}$) for the fluid transfer by dividing the accumulated mass-temperature product ($\dot{m}T_{accum}$) by the accumulated mass flow ($\dot{m}_{accum}$).

29. The method of claim 28, further comprising converting the non-aerated mass-weighted density ($\rho_{mass-weighted}$) to a standard density value using the non-aerated mass-weighted temperature ($T_{mass-weighted}$).

30. The method of claim 23, further comprising:
obtaining a viscosity ($\mu_i$) for the predetermined time portion ($t_i$);

if the predetermined time portion ($t_i$) is non-aerated, then adding a mass-viscosity product ($\dot{m}_i\mu_i$) to an accumulated mass-viscosity product ($\dot{m}\mu_{accum}$); and determining a non-aerated mass-weighted viscosity ($\mu_{mass\text{-}weighted}$) for the fluid transfer by dividing the accumulated mass-viscosity product ($\dot{m}\mu_{accum}$) by the accumulated mass flow ($\dot{m}_{accum}$).

31. The method of claim 30, with obtaining the viscosity ($\mu_i$) comprising receiving the viscosity ($\mu_i$) from an external source.

32. The method of claim 30, with obtaining the viscosity ($\mu_i$) comprising measuring the viscosity ($\mu_i$) with the vibratory flowmeter.

33. The method of claim 28, further comprising:
obtaining a viscosity ($\mu_i$) for the predetermined time portion ($t_i$);
if the predetermined time portion ($t_i$) is non-aerated, then adding a mass-viscosity product ($\dot{m}_i\mu_i$) to an accumulated mass-viscosity product ($\dot{m}\mu_{accum}$);
determining a non-aerated mass-weighted viscosity ($\mu_{mass\text{-}weighted}$) for the fluid transfer by dividing the accumulated mass-viscosity product ($\dot{m}\mu_{accum}$) by the accumulated mass flow ($\dot{m}_{accum}$); and
converting the non-aerated mass-weighted viscosity ($\mu_{mass\text{-}weighted}$) to a standard viscosity value using the non-aerated mass-weighted temperature ($T_{mass\text{-}weighted}$).

34. A fluid quantification method for a fluid being transferred, the method comprising measuring a mass flow ($\dot{m}_i$) for a predetermined time portion ($t_i$) of the fluid transfer, with the measuring being performed by a vibratory flowmeter, with the method being characterized by:
obtaining a viscosity ($\mu_i$) for the predetermined time portion ($t_i$);
determining if the fluid transfer is non-aerated during the predetermined time portion ($t_i$);
if the predetermined time portion ($t_i$) is non-aerated, then adding a mass-viscosity product ($\dot{m}_i\mu_i$) to an accumulated mass-viscosity product ($\dot{m}\mu_{accum}$) and adding the mass flow ($\dot{m}_i$) to an accumulated mass flow ($\dot{m}_{accum}$); and
determining a non-aerated mass-weighted viscosity ($\mu_{mass\text{-}weighted}$) for the fluid transfer by dividing the accumulated mass-viscosity product ($\dot{m}\mu_{accum}$) by the accumulated mass flow ($\dot{m}_{accum}$).

35. The method of claim 34, with determining the non-aerated mass-weighted viscosity ($\mu_{mass\text{-}weighted}$) for the fluid transfer occurring after a fluid transfer end signal is received.

36. The method of claim 34, with determining if the fluid transfer is non-aerated comprising:
comparing a vibrational response of the predetermined time portion ($t_i$) to a predetermined aeration threshold; and
determining the predetermined time portion ($t_i$) to be aerated if the vibrational response fails the predetermined aeration threshold.

37. The method of claim 36, further comprising:
totaling aerated time portions to obtain an aerated transfer time ($t_{aerated}$);
totaling all time portions ($t_i$) of the fluid transfer to obtain a total transfer time ($t_{total}$); and
determining an aeration fraction ($t_{aerated}/t_{total}$) as the aerated transfer time ($t_{aerated}$) divided by the total transfer time ($t_{total}$).

38. The method of claim 36, further comprising:
totaling aerated the mass flow ($\dot{m}_i$) values to obtain an aerated mass flow ($\dot{m}_{aerated}$);
totaling all mass flow ($\dot{m}_i$) values to obtain a total mass flow ($\dot{m}_{tot}$); and
determine an aeration fraction ($\dot{m}_{aerated}/\dot{m}_{tot}$) as the aerated mass flow ($\dot{m}_{aerated}$) divided by the total mass flow ($\dot{m}_{tot}$).

39. The method of claim 34, further comprising:
obtaining a temperature ($T_i$) for the predetermined time portion ($t_i$);
if the predetermined time portion ($t_i$) is non-aerated, then adding a mass-temperature product ($\dot{m}_i T_i$) to an accumulated mass-temperature product ($\dot{m}T_{accum}$); and
determining a non-aerated mass-weighted temperature ($T_{mass\text{-}weighted}$) for the fluid transfer by dividing the accumulated mass-temperature product ($\dot{m}T_{accum}$) by the accumulated mass flow ($\dot{m}_{accum}$).

40. The method of claim 39, further comprising converting the non-aerated mass-weighted viscosity ($\mu_{mass\text{-}weighted}$) to a standard viscosity value using the non-aerated mass-weighted temperature ($T_{mass\text{-}weighted}$).

41. The method of claim 34, further comprising:
measuring a density ($\rho_i$) for the predetermined time portion ($t_i$), with the measuring being performed by the vibratory flowmeter;
if the predetermined time portion ($t_i$) is non-aerated, then adding a mass-density product ($\dot{m}_i\rho_i$) to an accumulated mass-density product ($\dot{m}\rho_{accum}$); and
determining a non-aerated mass-weighted density ($\rho_{mass\text{-}weighted}$) for the fluid transfer by dividing the accumulated mass-density product ($\dot{m}\rho_{accum}$) by the accumulated mass flow ($\dot{m}_{accum}$).

42. The method of claim 39, further comprising:
measuring a density ($\rho_i$) for the predetermined time portion ($t_i$), with the measuring being performed by the vibratory flowmeter;
if the predetermined time portion ($t_i$) is non-aerated, then adding a mass-density product ($\dot{m}_i\rho_i$) to an accumulated mass-density product ($\dot{m}\rho_{accum}$);
determining a non-aerated mass-weighted density ($\rho_{mass\text{-}weighted}$) for the fluid transfer by dividing the accumulated mass-density product ($\dot{m}\rho_{accum}$) by the accumulated mass flow ($\dot{m}_{accum}$); and
converting the non-aerated mass-weighted density ($\rho_{mass\text{-}weighted}$) to a standard density value using the non-aerated mass-weighted temperature ($T_{mass\text{-}weighted}$).

43. The method of claim 34, with obtaining the viscosity ($\mu_i$) comprising receiving the viscosity ($\mu_i$) from an external source.

44. The method of claim 34, with obtaining the viscosity ($\mu_i$) comprising measuring the viscosity ($\mu_i$) with the vibratory flowmeter.

* * * * *